(12) United States Patent
Minamisono et al.

(10) Patent No.: US 8,703,954 B2
(45) Date of Patent: Apr. 22, 2014

(54) SALT OF TETRAHYDROTRIAZOLOPYRIDINE DERIVATIVE AND CRYSTAL THEREOF

(75) Inventors: Takuma Minamisono, Tsukuba (JP); Noritaka Kitazawa, Tsukuba (JP); Ikuo Kushida, Tuskuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 64 days.

(21) Appl. No.: 13/143,130

(22) PCT Filed: Feb. 24, 2010

(86) PCT No.: PCT/JP2010/053372
§ 371 (c)(1),
(2), (4) Date: Jul. 1, 2011

(87) PCT Pub. No.: WO2010/098490
PCT Pub. Date: Sep. 2, 2010

(65) Prior Publication Data
US 2011/0275822 A1 Nov. 10, 2011

(30) Foreign Application Priority Data
Feb. 26, 2009 (JP) ................. 2009-043268

(51) Int. Cl.
*C07D 471/04* (2006.01)
(52) U.S. Cl.
USPC ........................................ 546/119
(58) Field of Classification Search
USPC ........................................ 546/119
See application file for complete search history.

(56) References Cited

U.S. PATENT DOCUMENTS

| | | | |
|---|---|---|---|
| 7,618,960 B2 | 11/2009 | Kimura et al. | |
| 7,667,041 B2 | 2/2010 | Kimura et al. | |
| 7,687,640 B2 | 3/2010 | Kimura et al. | |
| 7,713,993 B2 | 5/2010 | Kimura et al. | |
| 7,880,009 B2 | 2/2011 | Kimura et al. | |
| 7,897,632 B2 | 3/2011 | Kimura et al. | |
| 7,935,815 B2 * | 5/2011 | Kimura et al. | 540/568 |
| 7,973,033 B2 | 7/2011 | Kimura et al. | |
| 8,008,293 B2 | 8/2011 | Kimura et al. | |
| 8,048,878 B2 | 11/2011 | Kimura et al. | |
| 2007/0219181 A1 | 9/2007 | Kimura et al. | |
| 2011/0009619 A1 * | 1/2011 | Kimura et al. | 540/568 |
| 2011/0065696 A1 | 3/2011 | Kimura et al. | |
| 2011/0086860 A1 | 4/2011 | Kimura et al. | |
| 2012/0135981 A1 | 5/2012 | Wu et al. | |

FOREIGN PATENT DOCUMENTS

| | | |
|---|---|---|
| EP | 1 992 618 A1 | 11/2008 |
| EP | 2 181 992 A1 | 5/2010 |
| UZ | 4 136 C | 4/2010 |
| UZ | 4 225 C | 9/2010 |
| WO | WO 2004/110350 A2 | 12/2004 |
| WO | WO-2007/102580 A1 | 9/2007 |
| WO | WO-2009/028588 A1 | 3/2009 |
| WO | 2010025197 * | 3/2010 |
| WO | WO 2010/025197 A1 | 3/2010 |
| WO | WO 2010/096488 A1 | 9/2010 |
| WO | WO 2010-097372 A1 | 9/2010 |
| WO | WO 2010-097395 A1 | 9/2010 |
| WO | WO 2010/098495 A1 | 9/2010 |

OTHER PUBLICATIONS

Singapore Search Report for Singapore Patent Application No. 201100985-9 dated May 10, 2012.
Singapore Written Opinion for Singapore Patent Application No. 201100985-9 dated May 7, 2012.
Amendment filed Dec. 7, 2011, in Singapore Patent Application No. 201105886-4.
Communication Pursuant to Rules 161(1) and 162 EPC issued Sep. 7, 2011, in European Patent Application No. 10708824.7.
Examination Report issued Jul. 19, 2012, in New Zealand Patent Application No. 594776.
International Preliminary Report on Patentability and Written Opinion issued Sep. 9, 2012, in PCT International Application No. PCT/JP2010/053368.
International Search Report issued Jul. 30, 2010, in PCT International Application No. PCT/JP2010/053368.

(Continued)

*Primary Examiner* — Niloofar Rahmani
(74) *Attorney, Agent, or Firm* — Birch, Stewart, Kolasch & Birch, LLP

(57) ABSTRACT

The present invention provides a crystal of a 1.5 D-tartrate of a compound represented by the formula (1) having an A production inhibitory effect, characterized in that the crystal has a diffraction peak at a diffraction angle (2θ.2) of 23.2 in powder X-ray diffractometry; a crystal of a disulfate of the compound of the formula (1), characterized in that the crystal has a diffraction peak at a diffraction angle (2θ.2) of 17.1 in powder X-ray diffractometry; various other salts of the compound of the formula (1); crystal polymorphs of these salts; and the like, which are expected to be used as drug substances.

(1)

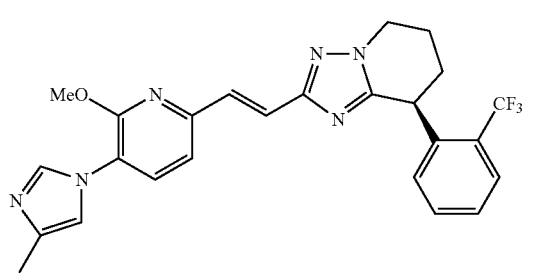

3 Claims, 4 Drawing Sheets

(56) References Cited

OTHER PUBLICATIONS

Request for the Correction of Error in the Specification issued Dec. 13, 2011, in Singapore Patent Application No. 201105886-4.
Response filed Feb. 6, 2012, in reply to the Request for the Correction of Error in the Specification issued Dec. 13, 2011, in Singapore Patent Application No. 201105866-4.
Response filed Nov. 10, 2011, in reply to the Official Communication Pursuant to Rules 161(1) and 162 EPC issued in European Patent Application No. 10708824.7.
Supplemental Response filed Feb. 6, 2012, in reply to the Official Communication Pursuant to Rules 161(1) and 162 EPC issued in European Patent Application No. 10708824.7.
Examiner's Report Issued on Patent of Invention Application issued Jun. 15, 2012, in Chilean Patent Application No. 2098-2011, with English translation.
Response filed Sep. 6, 2012, in reply to Examiner's Report Issued on Patent of Invention Application issued Jun. 15, 2012, in Chilean Patent Application No. 2098-2011, with English translation.
Amendment Order issued Jul. 17, 2012, in Thai Patent Application No. 1101001732, with English translation.
Communication pursuant to Article 94(3) dated Sep. 28, 2012 for European Patent Application No. 09791956.7.
Communication Under Rule 71(3) EPC issued Dec. 13, 2012, in European Patent Application No. 10708624.7.
Examiner's Report Issued on Patent of Invention Application issued Nov. 15, 2012, in Chilean Patent Application No. 2098-2011, with English translation.
Notification Before Examining Israeli Patent Application No. 214780 issued Nov. 13, 2012, with English translation.
Invitation to Respond to Written Opinion issued Dec. 18, 2012, in Singapore Patent Application No. 201105886-4.
Search Report issued Nov. 15, 2012, in Singapore Patent Application No. 201105886-4.
Written Opinion issued Nov. 15, 2012, in Singapore Patent Application No. 201105886-4.
Response filed Dec. 27, 2012 in reply to the Invitation to Respond to Written Opinion issued Dec. 18, 2012, in Singapore Patent Application No. 201105886-4.
Examination Report issued Dec. 7, 2012, in Pakistan Patent Application No. 143/2010.
Examination Report issued Dec. 7, 2012, in Pakistan Patent Application No. 657/2011.
Response filed Dec. 21, 2012, in reply to the Office Action issued Jul. 17, 2012, in Thai Patent Application No. 1101001732, with English translation.
First Office Action issued Jan. 25, 2013, in Chinese Patent Application No. 2010800092889, with English translation.
Communication Under Rule 71(3) EPC issued Dec. 12, 2012, in European Patent Application No. 08828870.9.
Extended European Search Report issued Jan. 22. 2013, in European Patent Application No. 19191398.2.
Notification to Go through Formalities of Registration issued Dec. 28, 2012, in Chinese Patent Application No. 200580020584.8, with English translation.
Official Letter and Search Report issued Jan. 29, 2013, in Taiwan Patent Application No. 97132893, with English translation.
Response filed Feb. 13, 2013, in reply to the First Examination Report issued Oct. 17, 2012, in Australian Patent Application No. 2008292390.
Response flied Janaury 22, 2013, in reply to the Subsequent Substantive Examination Report issued Nov. 23, 2012, in Philippine Patent Application No. 1-2010-500161.
Response filed Jan. 14, 2013, in reply to the First Office Action issued in Chinese Patent Application No. 200880104785.X, with English translation.
Response filed Jan. 15, 2013, in reply to the Official Notice of Results of the Substantive Examination No. 39629/SHTT-SC2 issued Nov. 26, 2012, in Vietnamese Patent Application No. 1-2010-00393, with English translation.
Response filed Jan. 16, 2013, in reply to the Substantive Examination Adverse Report issued Dec. 31, 2012, in Malaysian Patent Application No. PI 20052354.
Substantive Examination Adverse Report issued Dec. 31, 2012, in Malaysian Patent Application No. PI 20052354.
Response filed Feb. 15, 2013, in reply to the Office Action issued Nov. 15, 2012, in Chilean Patent Application No. 2098-2011, with English translation.
Request for Substantive Examination filed Jan. 25, 2013, in Indonesian Patent Application No. W-00 2011 03066, with English translation.
Response filed Mar. 4, 2013, in reply to the Request According to Section 18 issued Nov. 13, 2012, in Israeli Patent Application No. 214780, with English translation.
Replaced Search Report, mailed Feb. 1, 2013, for Singapore Application No. 201105886-4.
Replaced Written Opinion, mailed Feb. 1, 2013, for Singapore Application No. 201105886-4.
Response flied Apr. 12, 2013, in reply to the Communication Under Rule 71(3) EPC issued Dec. 13, 2012, in European Patent Application No. 10708824.7.
Communication Pursuant to Rules 161(1) and 162 EPC and Written Opinion issued Sep. 6, 2011, in European Patent Application No. 10708826.2.
Response filed Mar. 5, 2012, in reply to the Communication Pursuant to Rules 161(1) and 162 EPC and Written Opinion issued Sep. 6, 2011, in European Patent Application No. 10708826.2.
Official Action issued May 2, 2013, in Mexican Patent Application No. MX/a/2011/008501, with English translation.
Reply filed Sep. 23, 2013, in response to the Office Action issued May 30, 2013, in Israeli Patent Application No. 214780, with English translation.
Second Office Action issued Sep. 26, 2013, in Chinese Patent Application No. 201080009288.9, with English translation.
Invitation to Respond to Written Opinion issued May 23, 2013, in Singapore Patent Application No. 201105886-4.
Replaced Search Report issued May 3, 2013, in Singapore Patent Application No. 201105886-4.
Replaced Written Opinion issued May 3, 2013, in Singapore Patent Application No. 201105886-4.
Reply filed Jul. 10, 2013, in response to the Office Action issued May 2, 2013, in Mexican Patent Application No. MX/a/2011/008501, with English translation.
First Office Action isssued Feb. 5, 2013, in Chinese Patent Application No. 20108009393.2, with English translation.
Notice of Acceptance issued Mar. 25, 2013, in Australian Patent Application No. 2008292390.
Notice of the Result of Substantive Examination of a Patent Application issued Jun. 16, 2013, in GCC Patent Application No. 11619, with English translation.
Notification of Defects Prior to Allowance issued May 7, 2013, in Israeli Patent Application No. 203778, with English translation.
Notification of Reason for Rejection issued May 7, 2013, in Japanese Patent Application No. 2009-530168, with English translation.
Notification to Grant Patent Right issued Jun. 6, 2013, in Chinese Patent Application No. 200880104785.X, with english translation.
Office Action issued Jun. 25, 2013, in Mexican Patent Application No. MX/a/2010/002098, with English translation.
Office Action issued May 23, 2013, in Vietnamese Patent Application No. 1-2010-00393, with English translation.
Reply filed Jun. 24, 2013, in response to the Notification of Reason for Rejection issued May 7, 2013, in Japanese Patent Application No. 2009-530168, with English translation.
Reply filed May 10, 2013, in response to the response to the Substantive Examination Adverse Report issued Mar. 29, 2013, in Malayasian Patent Application No. PI 201000422.
Response filed Apr. 26, 2013, in Taiwan Patent Application No. 97132893, with English translation.
Substantive Examination Adverse Report issued Mar. 29, 2013, in Malaysian Patent Application No. PI 2010000422.
Substantive Examination Clear Report issued Jun. 14, 2013, in Malaysian Patent Application No. PI 20052354.

(56) References Cited

OTHER PUBLICATIONS

Reply filed Jun. 20, 2013, in Chinese Patent Application No. 201080009393.2, with English translation.
Official Action issued Aug. 16, 2013, in Russian Patent Application No. 201119132, with English translation.
Notice of Acceptance issued May 15, 2013, in New Zealand Patent Application No. 594776.
Communication pursuant to Article 94(3) EPC issued Jul. 30, 2013, in European Patent Application No. 05743758.4.
Notice Before Allowance issued Aug. 5, 2013, in Israeli Patent Application No. 203778, with English translation.
Notification of Defects issued Aug. 12, 2013, in Israeli Patent Application No. 213973, with English translation.
Notification of the Second Office Action issued Jul. 15, 2013, in Chinese Patent Application No. 201080009393.2, with English translation.
Office Action issued Aug. 23, 2013, in U.S. Appl. No. 12/974,447.
Response filed Aug. 13, 2013, in reply to the Invitation Pursuant to Rules 70a(2) and 70(2) EPC issued in European Patent Application No. 12191398.2.
Response filed Aug. 29, 2013, in reply to the Office Action issued Jun. 25, 2013, in Mexican Patent Application No. MX/a/2010/002098, with English translation of claims.
Response filed Jul. 25, 2013, in reply to the Office Action issued May 7, 2013, in Israeli Patent Application No. 203778, with English translation.
Response filed Oct. 15, 2013, in reply to the Official Action issued Aug. 16, 2013, in Russian Patent Application No. 2011139132, with English translation.
International Search Report, dated May 18, 2010 in PCT/JP2010/053372.
Extended European Scotch Report, issued Jun. 6, 2013, in Europeen Patent Application No. 13162886.9.
Amendment filed May 24, 2013, in response to the Office Action issued Jan. 25, 2013, in Chinese Patent Application No. 2010800092889, with English translation.
Notification of Defects issued May 30, 2013, in Israeli Patent Application No. 214780, with English translation.
Reply filed Nov. 14, 2013, in response to the Non-Final Office Action issued Aug. 23, 2013, in U.S. Appl. No. 12/974,447.
Notice of Allowance issued Dec. 13, 2013, in U.S. Appl. No. 12/974,447.
Reply filed Nov. 27, 2013, in response to the Office Action issued Jul. 30, 2013, in European Patent Application No. 05743758 4.
Response filed Dec. 8. 2013, in reply to the Office Action issued Aug. 12, 2013, in Israeli Patent Application No. 213973, with English translation.
Response filed Dec. 8, 2013, in reply to the Office Action issued Aug. 12, 2013, in Israeli Patent Application No. 213973, with English translation.
Response filed Jan. 17, 2014, in reply to the Office Action issued Jul. 22, 2013, in European Patent Application No. 13 162 886.9.
Communication Pursuant to Article 94(3) EPC issued Feb. 6, 2014, in European Patent Application No. 10 708 826 2.
Response to Second Office Action filed Dec. 11, 2013, in Chinese Patent Application No. 201080009288.9, with English translation.
Decision on Grant issued Nov. 1, 2013, in Russian Patent Application No. 2011139132/04(058436), with English translation.
Response filed Dec. 2, 2013, in response to the Office Action issued Jul. 15, 2013, in Chinese Patent Application No. 201080009393.2, with English translation.

\* cited by examiner

SALT OF TETRAHYDROTRIAZOLOPYRIDINE DERIVATIVE AND CRYSTAL THEREOF

This application is a National Phase of PCT/JP2010/053372 filed on Feb. 24, 2010, which claims priority under 35 USC 119(e) to U.S. Provisional Application No. 61/155,613 filed Feb. 26, 2009 and under 35 USC 119(a) to Patent Application No. 2009-043268 filed in Japan, on Feb. 26, 2009, all of which are hereby expressly incorporated by reference into the present application.

TECHNICAL FIELD

The present invention relates to a salt of a tetrahydrotriazolopyridine derivative, a solvate thereof and crystals of them that have an amyloid-β production reducing effect and are useful for the treatment of a neurodegenerative disease such as Alzheimer's disease or Down's syndrome.

BACKGROUND ART

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see NON-PATENT DOCUMENTS 1 and 2, for example). Aβ-proteins have, as main components, Aβ40 consisting of 40 amino acids and Aβ42 with two amino acids added at the C-terminal. The Aβ40 and Aβ42 are known to have high aggregability (see NON-PATENT DOCUMENT 3, for example) and to be main components of senile plaques (see NON-PATENT DOCUMENTS 4 and 5, for example). Further, it is known that the Aβ40 and Aβ42 are increased by mutation in APP and presenilin genes which is observed in familial Alzheimer's disease (see NON-PATENT DOCUMENTS 6, 7 and 8, for example). Accordingly, a compound that reduces the production of Aβ40 and Aβ42 is expected as a progression inhibitor or prophylactic agent for Alzheimer's disease.

PRIOR ART DOCUMENTS

Non-Patent Document

NON-PATENT DOCUMENT 1: Klein W L, et al., Alzheimer's disease-affected brain: Presence of oligomeric Aβ ligands (ADDLs) suggests a molecular basis for reversible memory loss, Proceeding National Academy of Science USA 2003, September 2; 100(18), p. 10417-10422.

NON-PATENT DOCUMENT 2: Nitsch R M, et al., Antibodies against β-amyloid slow cognitive declinein Alzheimer's disease, Neuron, 2003, May 22; 38, p. 547-554.

NON-PATENT DOCUMENT 3: Jarrett J T, et al., The carboxy terminus of the β amyloid protein is critical for the seeding of amyloid formation: Implications for the pathogenesis of Alzheimers' disease, Biochemistry, 1993, 32(18), p. 4693-4697.

NON-PATENT DOCUMENT 4: Glenner G G, et al., Alzheimer's disease: initial report of the purification and characterization of a novel cerebrovascular amyloid protein, Biochemical and biophysical research communications, 1984, May 16, 120(3), p. 885-890.

NON-PATENT DOCUMENT 5: Masters C L, et al., Amyloid plaque core protein in Alzheimer disease and Down syndrome, Proceeding National Academy of Science USA, 1985, June, 82(12), p. 4245-4249.

NON-PATENT DOCUMENT 6: Gouras G K, et al., Intraneuronal Aβ42 accumulation in human brain, American Journal of Pathology, 2000, January, 156(1), p. 15-20.

NON-PATENT DOCUMENT 7: Scheuner D, et al., Secreted amyloid β-protein similar to that in thesenile plaques of Alzheimer's disease is increased in vivo by the presenilin 1 and 2 and APP mutations linked to familial Alzheimer's disease, Nature Medicine, 1996, August, 2(8), p. 864-870.

NON-PATENT DOCUMENT 8: Forman M S, et al., Differential effects of the swedish mutant amyloid precursor protein on β-amyloid accumulation and secretion in neurons and normeuronal cells, The Journal of Biological Chemistry, 1997, Dec. 19, 272(51), p. 32247-32253.

SUMMARY OF THE INVENTION

Problems to be Solved by the Invention

As a novel compound that has an effect of reducing the production of Aβ40 and 42 and is expected as a therapeutic or prophylactic agent for Alzheimer's disease or the like, the present inventors have found a compound represented by the following formula (1) (compound (1)):

[Formula 1]

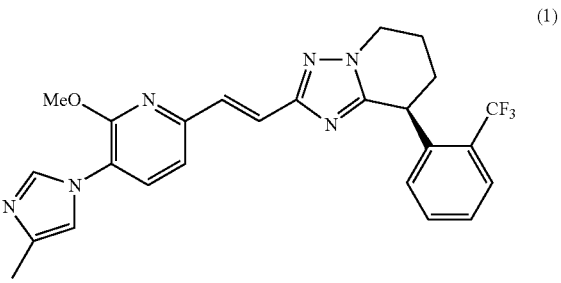

(1)

and filed a patent application for the invention (PCT/JP08/065,365).

Generally, properties of salts of compounds and those crystals that are useful as pharmaceuticals are highly important for the development of pharmaceuticals, because the properties greatly affect bioavailability of drugs, purity of drug substances, formulation of preparations, and the like. Therefore, it is necessary to research which salts and crystal forms of the compound of the formula (1) are most excellent as pharmaceuticals. Specifically, since their properties depend on the character of the individual compounds, it is generally difficult to estimate salts and crystal forms for drug substances having excellent properties and it is demanded to actually make various studies for each compound.

Accordingly, an object of the present invention is to provide a salt and a crystal form of the compound represented by the formula (1), which have excellent properties as drug substances.

Means for Solving the Problems

The present inventors have isolated various salts and crystal forms of the compound represented by the formula (1): (8S)-2-{(E)-2-[6-methoxy-5-(4-methyl-1H-imidazol-1-yl) pyridin-2-yl]vinyl}-8-[2-(trifluoromethyl)phenyl]-5,6,7,8-tetrahydro[1,2,4]triazolo[1,5-a]pyridine (compound (1)), understood their properties and morphology and made extensive studies. As a result, the inventors have found salts, crystal forms and the like for drug substances having excellent properties. This finding has led to the completion of the present invention.

Specifically, the present invention relates to:

[1]. A salt comprising one acid selected from the group consisting of an inorganic acid, an organic carboxylic acid and an organic sulfonic acid and (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine, or a solvate thereof;

[2]. The salt or the solvate thereof according to [1] above, wherein the acid is an organic carboxylic acid;

[3]. The salt or the solvate thereof according to [1] or [2] above, wherein the organic carboxylic acid is acetic acid, oxalic acid, maleic acid, tartaric acid, malonic acid, fumaric acid or citric acid;

[4]. The salt or the solvate thereof according to [1] above, wherein the acid is an organic sulfonic acid;

[5]. The salt or the solvate thereof according to [1] or [4] above, wherein the organic sulfonic acid is methanesulfonic acid, trifluoromethanesulfonic acid, ethanesulfonic acid, benzenesulfonic acid, toluenesulfonic acid or camphorsulfonic acid;

[6]. The salt or the solvate thereof according to [1] above, wherein the acid is an inorganic acid;

[7]. The salt or the solvate thereof according to [1] or [6] above, wherein the inorganic acid is hydrochloric acid, hydrobromic acid, sulfuric acid or phosphoric acid;

[8]. A crystal of a free form of (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine, or a crystal of the salt or the solvate thereof according to any one of [1] to [7] above;

[9]. A crystal of (8S)-2-{(E)-2-[6-methoxy-5-(4-methyl-1H-imidazol-1-yl)pyridin-2-yl]vinyl}-8-[2-(trifluoromethyl) phenyl]-5,6,7,8-tetrahydro[1,2,4]triazolo[1,5-a]pyridine 1.5 D-tartrate having diffraction peaks at diffraction angles (2θ±0.2°) of 12.6° and 23.2° in powder X-ray diffractometry; and

[10]. A crystal of (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine disulfate having diffraction peaks at diffraction angles (2θ±0.2°) of 17.1° and 24.0° in powder X-ray diffractometry.

Advantages of the Invention

A salt of (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (compound (1)), a solvate thereof, crystals of the compound, the salt and the solvate, and the like provided by the present invention have excellent properties as drug substances for pharmaceuticals.

EMBODIMENT FOR CARRYING OUT THE INVENTION

Figure 1:
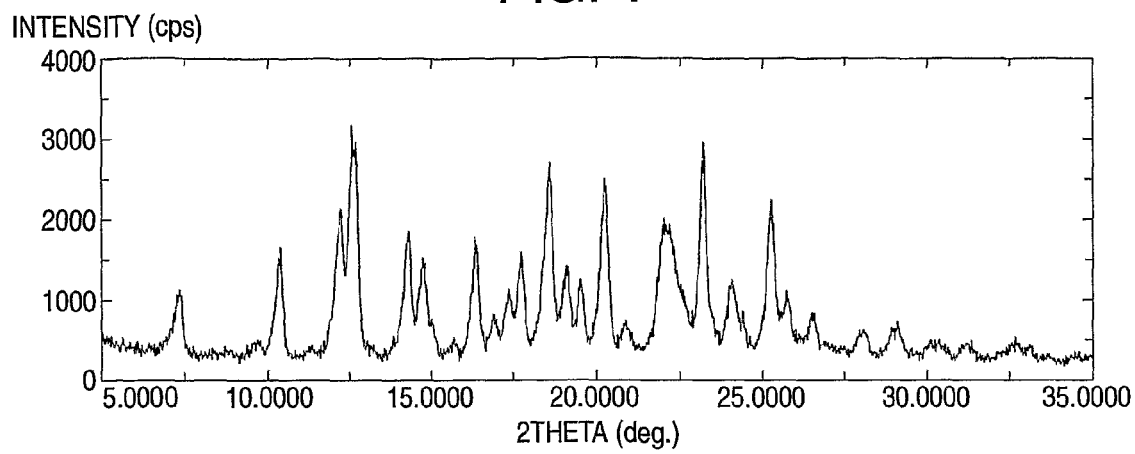
FIG. 1 is the powder X-ray diffraction pattern of a crystal of a 1.5 D-tartrate of (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (compound (1)) obtained in Example 1. The horizontal axis shows a diffraction angle (2θ) and the vertical axis shows a peak strength.
Figure 2:
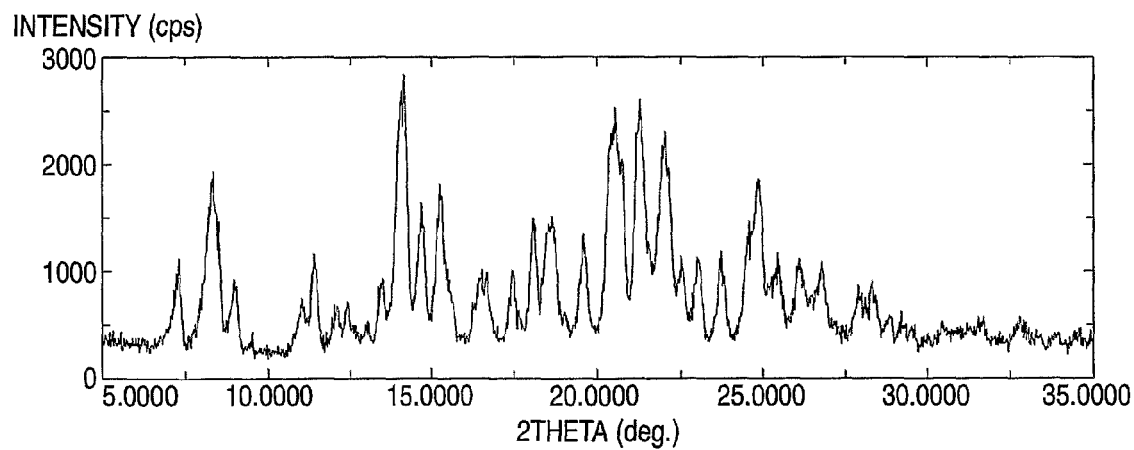
FIG. 2 is the powder X-ray diffraction pattern of a crystal of compound (1) di-D-tartrate obtained in Example 2. The horizontal axis shows a diffraction angle (2θ) and the vertical axis shows a peak strength.
Figure 3:
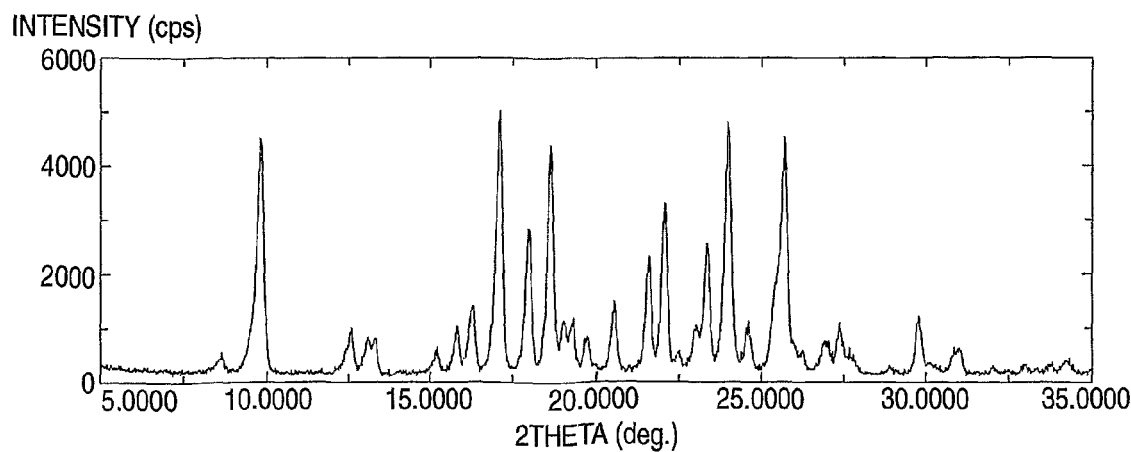
FIG. 3 is the powder X-ray diffraction pattern of a crystal of compound (1) disulfate obtained in Example 3. The horizontal axis shows a diffraction angle (2θ) and the vertical axis shows a peak strength.
Figure 4:
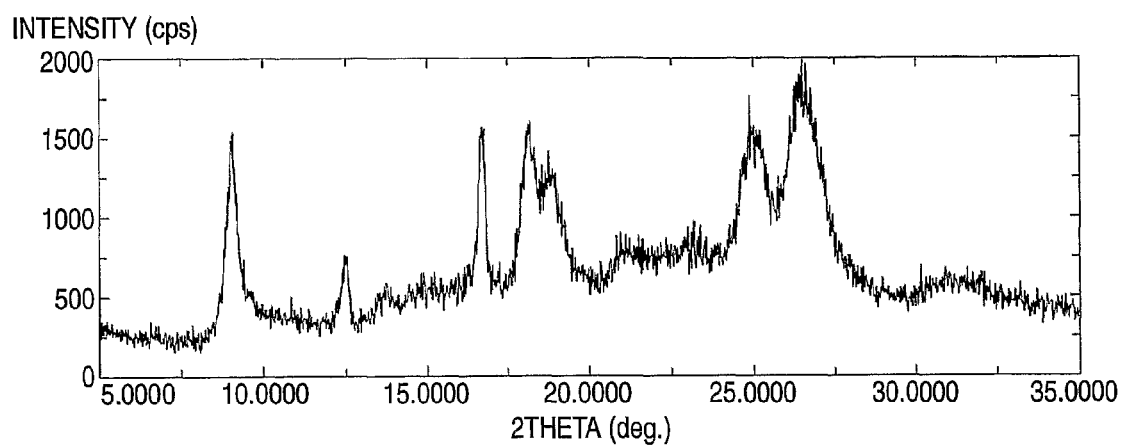
FIG. 4 is the powder X-ray diffraction pattern of a crystal of compound (1) dihydrobromide obtained in Example 4. The horizontal axis shows a diffraction angle (2θ) and the vertical axis shows a peak strength.
Figure 5:
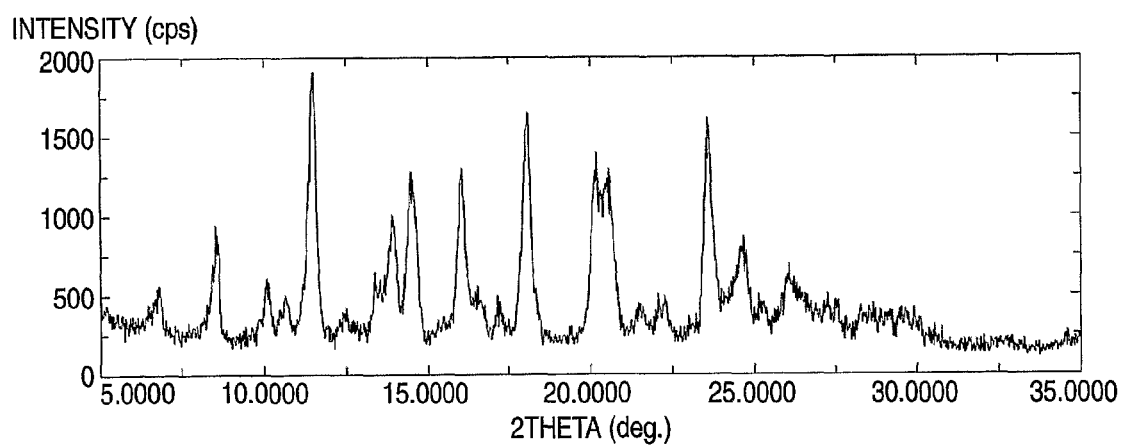
FIG. 5 is the powder X-ray diffraction pattern of a crystal of compound (1) hydrochloride obtained in Example 5. The horizontal axis shows a diffraction angle (2θ) and the vertical axis shows a peak strength.
Figure 6:
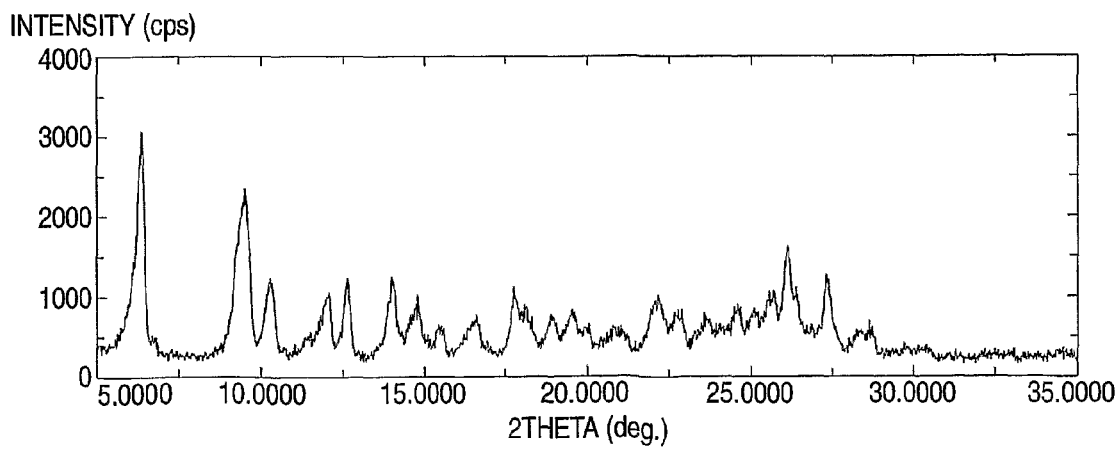
FIG. 6 is the powder X-ray diffraction pattern of a crystal of compound (1) hydrochloride obtained in Example 6. The horizontal axis shows a diffraction angle (2θ) and the vertical axis shows a peak strength.
Figure 7:
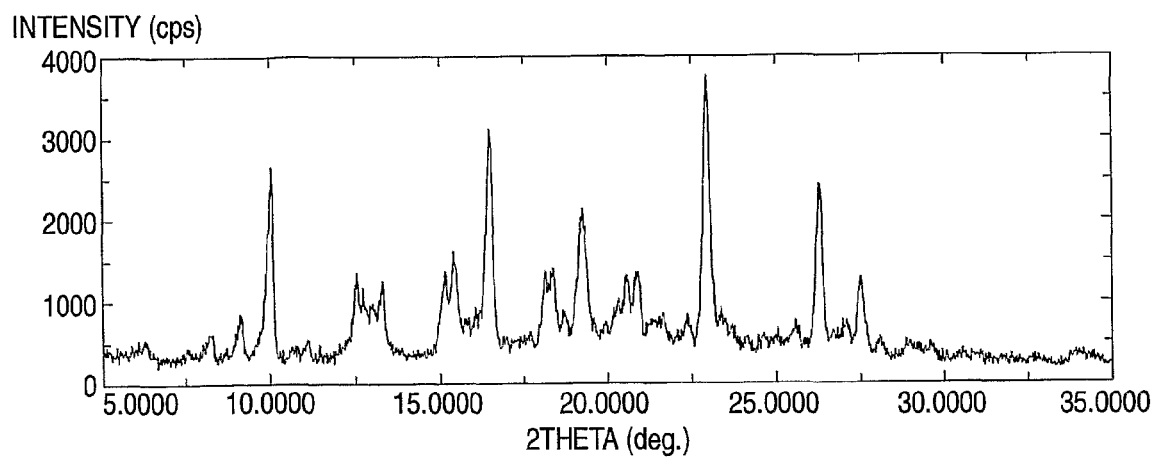
FIG. 7 is the powder X-ray diffraction pattern of a crystal of compound (1) mesylate obtained in Example 7. The horizontal axis shows a diffraction angle (2θ) and the vertical axis shows a peak strength.
Figure 8:
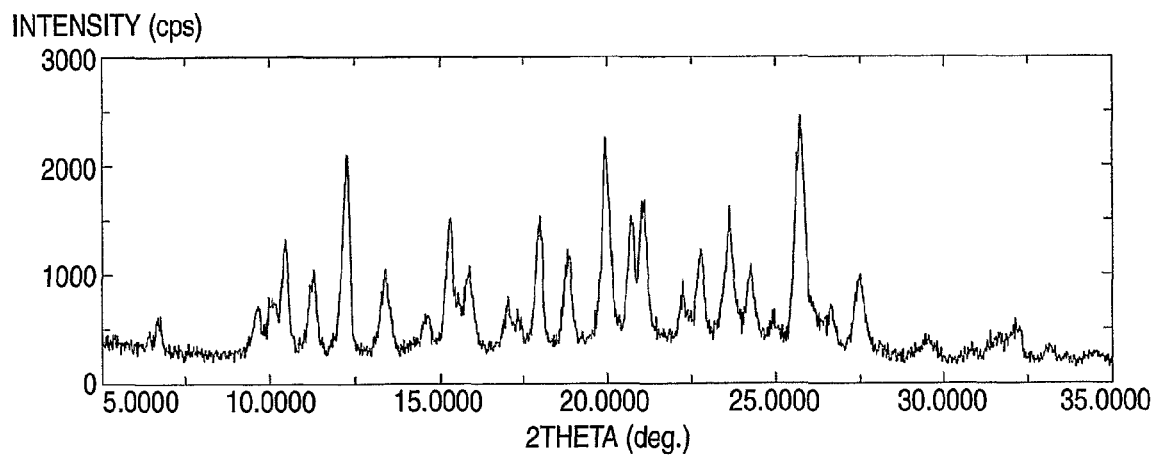
FIG. 8 is the powder X-ray diffraction pattern of a crystal of compound (1) diphosphate obtained in Example 8. The horizontal axis shows a diffraction angle (2θ) and the vertical axis shows a peak strength.
Figure 9:
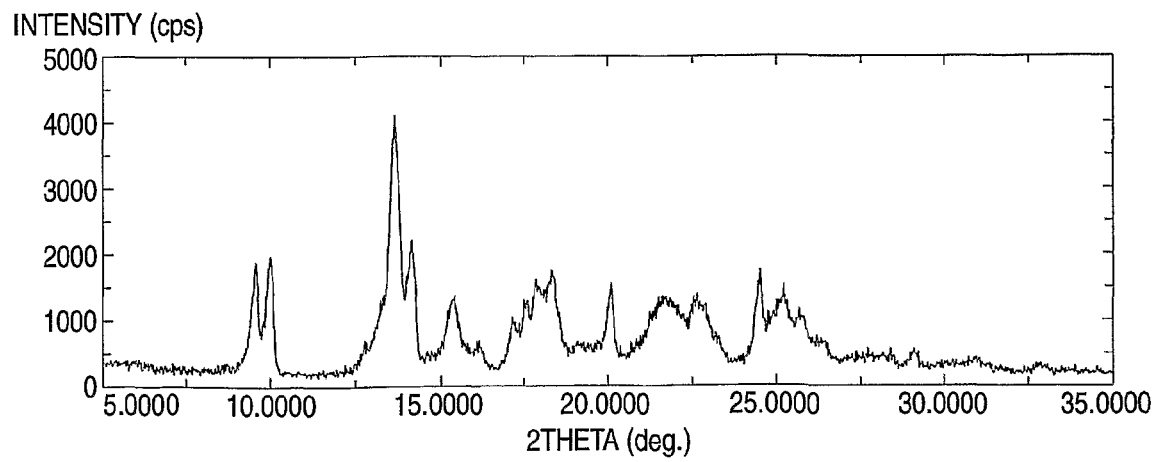
FIG. 9 is the powder X-ray diffraction pattern of a crystal of compound (1) diphosphate obtained in Example 9. The horizontal axis shows a diffraction angle (2θ) and the vertical axis shows a peak strength.
Figure 10:
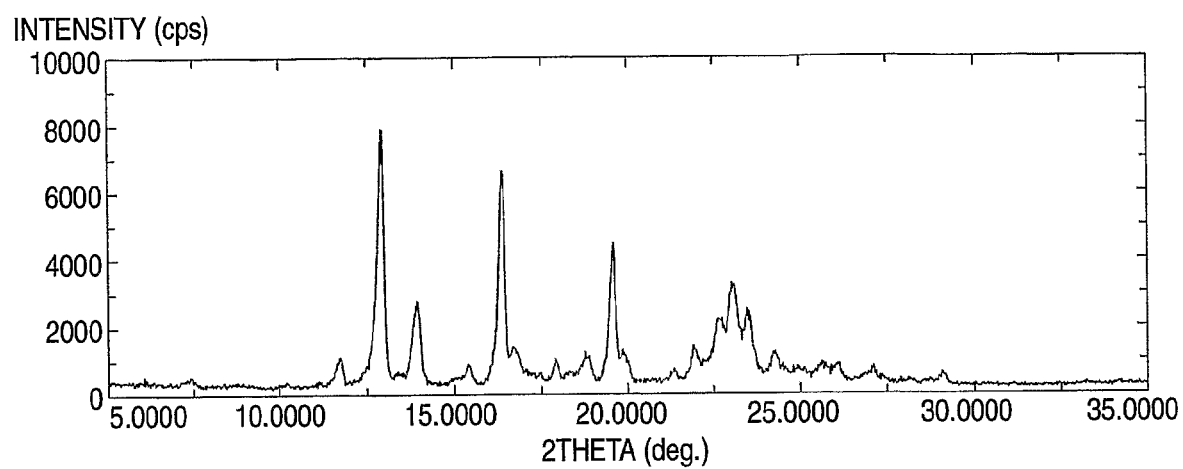
FIG. 10 is the powder X-ray diffraction pattern of a crystal of compound (1) free form obtained in Reference Example 1. The horizontal axis shows a diffraction angle (2θ) and the vertical axis shows a peak strength.

Next, the salt, the solvate, the crystals and the like and the methods for producing them according to the present invention will be described in detail.

In the present invention, the "salt" refers to a pharmacologically acceptable salt, and means a pharmacologically acceptable salt formed by the compound (I) as a prophylactic or therapeutic agent for a disease caused by Aβ together with an acid. In the present invention, the "salt" is not limited to examples described in the present specification, and refers to a compound generated by reaction of the compound (1) with a chemically possible number of equivalents of an acid and formed of a base positive moiety and an acid negative moiety.

Specifically, the salt of the present invention is a salt comprising one acid selected from the group consisting of an inorganic acid, an organic carboxylic acid and an organic sulfonic acid and the compound (1).

Preferable examples of the inorganic acid include hydrofluoric acid, hydrochloric acid, hydrobromic acid, hydroiodic acid, sulfuric acid, nitric acid, perchloric acid, phosphoric acid, carbonic acid and bicarbonic acid. More preferable examples of the inorganic acid include hydrochloric acid, hydrobromic acid, sulfuric acid, nitric acid and phosphoric acid. Preferable examples of the organic carboxylic acid include acetic acid, oxalic acid, maleic acid, tartaric acid, fumaric acid, citric acid and malonic acid. More preferable examples of the organic carboxylic acid include maleic acid, tartaric acid, fumaric acid and malonic acid. Preferable examples of the organic sulfonic acid include methanesulfonic acid, trifluoromethanesulfonic acid, ethanesulfonic acid, benzenesulfonic acid, toluenesulfonic acid and camphorsulfonic acid. More preferable examples of the organic sulfonic acid include methanesulfonic acid and toluenesulfonic acid.

In the present invention, the solvate refers to a solid formed by the salt of the compound (1) together with a solvent molecule. Examples of the solvate include a hydrate formed by the salt of the compound (1) and a water molecule; an alcoholate formed by the salt of the compound (1) and an alcohol molecule such as methanol, ethanol, 1-propanol or 2-propanol; a solvate formed by the salt of the compound (1) and a polar solvent such as 1-methyl-2-pyrrolidone, N,N-dimethylformamide or dimethyl sulfoxide; a solvate formed by the salt of the compound (1) and an ester solvent such as ethyl acetate or methyl acetate; and a solvate formed by the salt of the compound (1) and a ketone solvent such as acetone, butanone or cyclohexanone.

In the present invention, the crystal refers to a crystal of a salt of the compound (1), or a crystal of a solvate of the salt of the compound (1).

In the present invention, preferable examples of the crystal typically include:

a crystal of compound (1) 1.5 D-tartrate having diffraction peaks at diffraction angles (2θ±0.2°) of 12.6° and 23.2° in powder X-ray diffractometry;

in particular, a crystal of compound (1) 1.5 D-tartrate having diffraction peaks at diffraction angles (2θ±0.2°) of 12.6°, 18.6°, 20.2°, 23.2° and 25.2° in powder X-ray diffractometry;

a crystal of compound (1) disulfate having diffraction peaks at diffraction angles (2θ±0.2°) of 17.1° and 24.0° in powder X-ray diffractometry; and in particular, a crystal of compound (1) disulfate having diffraction peaks at diffraction angles (2θ±0.2°) of 9.8°, 17.1°, 18.7°, 24.0° and 25.7° in powder X-ray diffractometry.

Preferable examples of the crystal also include crystals of various other salts; and crystals of solvates of those salts.

Generally, a diffraction angle (2θ) in powder X-ray diffractometry may have an error in the range of ±0.2°. Therefore, the above-described diffraction angle values should be understood as including values in the range of about ±0.2°. Accordingly, the present invention includes not only crystals whose peak diffraction angles in powder X-ray diffractometry completely coincide with each other, but also crystals whose peak diffraction angles coincide with each other with an error of about ±0.2°.

Therefore, in the present invention, the phrase "having a diffraction peak at a diffraction angle (2θ±0.2°) of 12.6°" means "having a diffraction peak at a diffraction angle (2θ) of 12.4° to 12.8°", for example; the same applies to other diffraction angles.

The methods for producing the compound (1), the salt thereof, the solvate of the salt, the crystals of the compound, the salt and the solvate, and the like according to the present invention will be described below in detail.

Production of Compound (1)

As specifically described later in Reference Example 1, the compound (1) according to the present invention can be synthesized from 1-amino-3-(2-trifluoromethylphenyl)piperidin-2-one as a starting material through (E)-3-[6-methoxy-5-(4-methyl-1H-imidazol-1-yl)pyridin-2-yl]-N-[2-oxo-3-(2-trifluoromethylphenyl)piperidin-1-yl]acrylamide.

Method for Producing Salt of Compound (1)

The salt of the compound (1) can be obtained by a conventional method for producing a salt. Specifically, for example, the salt can be produced by dissolving the compound (1) in a solvent with heating as necessary; then adding one acid selected from the group consisting of an inorganic acid, an organic carboxylic acid and an organic sulfonic acid to the resulting solution; and stirring the mixture for several minutes to several hours at room temperature or with cooling in an ice bath or leaving the mixture to stand for several minutes to several hours at room temperature or with cooling in an ice bath. The salt of the compound (1) can be obtained as a crystalline or amorphous form by this production method. Examples of the solvent used here include alcohol solvents such as ethanol, 1-propanol and 2-propanol; alkyl ketone solvents such as acetone and 2-butanone; ethyl acetate; hexane; acetonitrile, and mixed solvents thereof.

The salt of the compound (1) can also be produced by synthesizing the compound (1) by the above-described method for producing the compound (1) and subsequently employing the above-described method.

Method for Producing Solvate of Salt of Compound (1)

The solvate of the salt of the compound (1) can be produced by dissolving the compound (1) in a solvent with heating as necessary; then adding an acid with further addition of a solvent of the solvate to be obtained; and stirring the mixture for several minutes to several hours at room temperature or with cooling in an ice bath or leaving the mixture to stand for several minutes to several hours at room temperature or with cooling in an ice bath in the above-described method for producing the salt of the compound (1), for example. In order to obtain a solvate of the solvent first used for dissolving the compound (1), it is not necessary to further add another solvent. The target solvate can be obtained by stirring the mixture or leaving the mixture to stand as is. The solvate of the salt of the compound (1) can be obtained as a crystalline or amorphous form by this production method.

The solvate of the salt of the compound (1) can also be produced by synthesizing the compound (1) by the above-described method for producing the compound (1) and subsequently employing the above-described method for producing the salt of the compound (1) and the above-described method.

Method for Producing Crystalline Salts of Compound (1) and Solvates of the Salts Crystalline salts of the compound (1) and the solvates of the salts can be produced by dissolving the free form of the compound (1), the salt thereof or the solvate of the salt by heating in a solvent, cooling the solution with stirring, and carrying out crystallization.

The salt of the compound (1) or the solvate of the salt used for crystallization may have any form, specifically, may be either a hydrate or an anhydride, either an amorphous form or a crystalline form (including a crystalline form formed of a plurality of crystal polymorphs), or a mixture thereof.

Examples of the solvent used for crystallization include alcohol solvents such as methanol, ethanol, 2-propanol and n-propanol; acetonitrile; amide solvents such as N,N-dimethylformamide; ester solvents such as ethyl acetate; saturated hydrocarbon solvents such as heptane; and mixed solvents thereof.

The amount of the solvent used may be appropriately selected between an amount that allows the free form of the compound (1), the salt thereof or the solvate of the salt to be dissolved by heating as a lower limit and an amount that does not significantly reduce the yield of the crystals as an upper limit.

The crystal obtained by the above-described method is formed of a single crystal form. The crystal form is stable, is not easily transformed into another crystal form or amorphous form, has excellent properties such as nonhygroscopicity and is also suitable for formulation.

The temperature for dissolving the free form of the compound (1), the salt thereof or the solvate of the salt by heating may be appropriately selected according to the solvent so that the compound (1) can be dissolved. The temperature is preferably the reflux temperature of the recrystallization solvent to 50° C., and more preferably 65 to 55° C.

Rapid cooling during crystallization results in crystals including those having different forms (polymorphs). Therefore, it is preferable to carry out crystallization with the cooling temperature appropriately controlled taking an influence on the quality, the grain size and the like of the crystals into consideration. Slow cooling (cooling at a rate of 30 to 5° C./hour) is preferable. The cooling temperature is more preferably 30 to 20° C./hour.

The final crystallization temperature may be appropriately selected according to the yield, the quality and the like of the crystals and is preferably room temperature to 60° C., for example.

The target crystals can be obtained by separating the crystallized crystals by a conventional filtration operation, washing the separated crystals with a solvent as necessary and further drying the crystals. Many of the solvents used for washing the crystals are the same as the crystallization solvents.

The crystals separated by a filtration operation can be appropriately dried by leaving the crystals to stand in the air or in a nitrogen stream or by heating the crystals.

The drying time may be appropriately selected as a time until the amount of the residual solvent is below a predetermined amount according to the production amount, the drying device, the drying temperature and the like. The drying can be carried out under ventilation or under reduced pressure. The degree of pressure reduction may be appropriately selected according to the production amount, the drying device, the drying temperature and the like. The resulting crystals may be left to stand in the air as necessary after drying.

The above-described crystals can also be produced by synthesizing the compound (1) by the above-described method for producing the compound (1) and subsequently employing the above-described method, or by synthesizing the compound (1) and subsequently employing the above-described method for producing the salt of the compound (1) or the solvate.

The salt of the compound (1), the solvate thereof, the crystals of the compound, the salt and the solvate, and the like obtained by the production methods described above have an Aβ production reducing effect and can be used as an active ingredient in a therapeutic agent for a neurodegenerative disease caused by Aβ such as Alzheimer's disease or Down's syndrome.

The salt of the compound (1), the solvate thereof, the crystals of the compound, the salt and the solvate, and the like used as a drug are orally or parenterally administered as a therapeutic agent for a neurodegenerative disease caused by Aβ such as Alzheimer's disease or Down's syndrome, for example. The dose varies according to the degree of symptom, the age, sex and weight of the patient, the difference in sensitivity among the patients, the administration method, the administration period, the administration interval, the character, formulation and type of the pharmaceutical preparation, and the type of the active ingredient, for example, and is not particularly limited. The dose is usually 10 to 6000 mg per adult per day, preferably about 50 to 4000 mg per adult per day, and still more preferably about 100 to 3000 mg per adult per day, for example, and is usually administered in one to three divided doses per day.

An oral solid preparation is prepared by adding an excipient and, as necessary, a binder, a disintegrant, a lubricant, a colorant, a corrective and the like to the principal agent, and then formulating tablets, coated tablets, granules, fine granules, powder or capsules, for example, by a conventional method. Examples of the expicient used include lactose, corn starch, sucrose, glucose, sorbitol, crystalline cellulose and silicon dioxide. Examples of the binder used include polyvinyl alcohol, ethylcellulose, methylcellulose, gum arabic, hydroxypropylcellulose and hydroxypropylmethylcellulose. Examples of the lubricant used include magnesium stearate, talc and silica. Examples of the colorant used include those permitted to be added to pharmaceuticals. Examples of the corrective used include cacao powder, menthol, aromatic acid, peppermint oil, borneol and cinnamon powder. These tablets or granules may be appropriately coated with sugar, gelatin or other coatings as necessary, obviously. An injection is prepared by adding a pH adjuster, a buffer, a suspending agent, a solubilizer, a stabilizer, an isotonizing agent and a preservative, for example, to the principal agent as necessary and formulating an intravenous, subcutaneous or intramuscular injection, for example, by a conventional method. In this case, the injection may be formulated as a lyophilized product by a conventional method. Examples of the suspending agent include methylcellulose, polysolvate 80, hydroxyethylcellulose, gum arabic, tragacanth powder, sodium carboxymethylcellulose and polyoxyethylene sorbitan monolaurate.

EXAMPLES

The present invention will be described in detail below with reference to reference examples and examples; however, the present invention is not limited to these reference examples and examples.

The following abbreviations are used in the following reference examples and examples.

DMF: N,N'-dimethylformamide
THF: Tetrahydrofuran
EDC: 1-Ethyl-3-(3-dimethylaminopropyl)carbodiimide hydrochloride
HOBT: 1-Hydroxybenzotriazole
IPEA: Diisopropylethylamine In powder X-ray diffractometry of the crystals produced in the following examples, the resulting crystals were placed on a sample stage of a powder X-ray diffractometer and analyzed under the following conditions.

Measurement Conditions
    Sample holder: Aluminum
    Target: Copper
    Detector: Scintillation counter
    Tube voltage: 50 kV
    Tube current: 300 mA
    Slit: DS 0.5 mm (Height limiting slit 2 mm), SS Open, RS Open
    Scanning rate: 5°/min
    Sampling interval: 0.02°
    Scan range: 5 to 35°
    Goniometer: Horizontal goniometer

Reference Example 1

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine

[Formula 2]

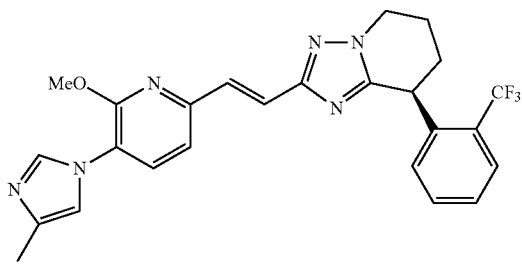

Synthesis of 1-amino-3-(2-trifluoromethylphenyl)piperidin-2-one

Thionyl chloride (2.72 mL) was added to a solution of 2-trifluoromethylphenylacetic acid (1.9 g) in methanol (38 mL), followed by stirring at room temperature for three hours. The reaction solution was concentrated under reduced pressure. The resulting residue was diluted with DMF. Sodium hydride (containing 40% mineral oil, 410 mg) was added under ice-cooling, followed by stirring for 10 minutes. The reaction solution was further stirred for 30 minutes and then ice-cooled again. 1-Chloro-3-iodopropane (1.02 mL) was added to the reaction mixture, and the reaction solution was stirred at room temperature overnight. Water and ethyl acetate were added to the reaction mixture, and the organic layer was separated. The resulting organic layer was washed with saturated aqueous sodium chloride, dried over anhydrous magnesium sulfate and then concentrated under reduced pressure. The resulting residue was diluted with ethanol (26.6 mL). Hydrazine monohydrate (7.6 mL) was added, and the reaction solution was stirred at room temperature for two hours and then at 60° C. for further three hours. The reaction mixture was concentrated under reduced pressure. Saturated aqueous sodium bicarbonate and ethyl acetate and were added to the residue, and the organic layer was separated. The resulting organic layer was washed with saturated aqueous sodium chloride, dried over anhydrous magnesium sulfate and then concentrated under reduced pressure. The residue was purified by silica gel column chromatography (carrier: Chromatorex NH; elution solvent: heptane-ethyl acetate system) to obtain 1.68 g of the title compound. The property values of the compound are as follows.

ESI-MS; m/z 259 [M$^+$+H]. $^1$H-NMR (CDCl$_3$) δ (ppm): 1.82-2.10 (m, 3H), 2.18-2.26 (m, 1H), 3.58-3.76 (m, 2H), 4.07 (dd, J=10.0, 5.6 Hz, 1H), 4.60 (s, 2H), 7.24 (d, J=7.6 Hz, 1H), 7.35 (t, J=7.6 Hz, 1H), 7.51 (t, J=7.6 Hz, 1H), 7.66 (d, J=7.6 Hz, 1H).

Synthesis of (E)-3-[6-methoxy-5-(4-methyl-1H-imidazol-1-yl)pyridin-2-yl]-N-[2-oxo-3-(2-trifluoromethylphenyl)piperidin-1-yl]acrylamide EDC (834 mg), HOBT (588 mg) and IPEA (2.03 mL) were added to a suspension of (E)-3-[6-methoxy-5-(4-methyl-1H-imidazol-1-yl)pyridin-2-yl]acrylic acid trifluoroacetate (1.42 g) and 1-amino-3-(2-trifluoromethylphenyl)piperidin-2-one (750 mg) in DMF (30 mL). After stirring at room temperature for 14 hours, a saturated sodium bicarbonate solution and ethyl acetate were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate-methanol system) to obtain 1.23 g of the title compound. The property values of the compound are as follows.

ESI-MS; m/z 500 [M$^+$+H].

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Phosphorus oxychloride (24.2 mL) was added to (E)-3-[6-methoxy-5-(4-methyl-1-imidazol-1-yl)pyridin-2-yl]-N-[2-oxo-3-(2-trifluoromethylphenyl)piperidin-1-yl]acrylamide (1.2 g). The reaction solution was stirred at 100° C. for one hour and then concentrated under reduced pressure. Subsequently, the residue was diluted with acetic acid (24.2 mL) and then ammonium acetate (1.9 g) was added, followed by stirring at 150° C. for two hours. The reaction solution was left to cool to room temperature and then concentrated under reduced pressure. A saturated sodium bicarbonate solution and ethyl acetate were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane-ethyl acetate system) to obtain a racemate of the title compound (750 mg). The resulting racemate (410 mg) was separated by CHIRALPAK™ IA manufactured by Daicel Chemical Industries, Ltd. (2 cm×25 cm, mobile phase: hexane:ethanol=8:2, flow rate: 10 mL/min) to obtain the title compound with a retention time of 33 minutes and negative optical rotation (170 mg) as crystals.

The property values of the title compound are as follows.
$^1$H-NMR (CDCl$_3$) δ (ppm): 1.90-2.01 (m, 1H), 2.10-2.35 (m, 2H), 2.29 (d, J=1.2 Hz, 3H), 2.42-2.51 (m, 1H), 4.03 (s, 3H), 4.28-4.41 (m, 2H), 4.70 (dd, J=8.4, 6.0 Hz, 1H), 6.92 (d, J=8.0 Hz, 1H), 6.95 (t, J=1.2 Hz, 1H), 7.01 (d, J=7.6 Hz, 1H), 7.39 (t, J=7.6 Hz, 1H), 7.44 (d, J=16.0 Hz, 1H), 7.45 (d, J=8.0 Hz, 1H), 7.49 (t, J=7.6 Hz, 1H), 7.63 (d, J=16.0 Hz, 1H), 7.72 (d, J=7.6 Hz, 1H), 7.76 (d, J=1.2 Hz, 1H).

(8S)-2-{(E)-2-[6-Methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine synthesized according to the above reference example was used for the following synthesis of salts.

Example 1

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine 1.5 D-tartrate (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (33.70 mg) was dissolved in 285 μL of a D-tartaric acid-ethanol solution (110.92 mg/3 mL) with stirring at room temperature. The oil was precipitated when 1 mL of heptane was added. Accordingly, the oily substance was dissolved by adding 1 mL of ethanol. Further, 0.5 mL of heptane was added, and the mixture was transferred to a low temperature laboratory at about 5° C. (under shading) and continuously stirred for 24 hours. Thus, partial gelation occurred. Thereafter, the mixture was brought back to room temperature and continuously stirred, resulting in precipitation of a solid. The solid was collected by filtration through a glass filter and dried under reduced pressure at room temperature to obtain 21.25 mg of the title compound as white solid crystals.

$^1$H-NMR (600 MHz, DMSO-$d_6$) δ (ppm): 1.96 (m, 1H), 2.14 (s, 3H), 2.16 (m, 2H), 2.29 (m, 1H), 3.98 (s, 3H), 4.28 (m, 2H), 4.29 (s, 3H), 4.51 (dd, J=9, 6 Hz, 1H), 7.22 (s, 1H), 7.25 (brd, J=8 Hz, 1H), 7.27 (d, J=8 Hz, 1H), 7.32 (d, J=16 Hz, 1H), 7.46 (d, J=16 Hz, 1H), 7.49 (brdd, J=8 Hz, 1H), 7.61 (brdd, J=8 Hz, 1H), 7.77 (brd, J=8 Hz, 1H), 7.78 (d, J=8 Hz, 1H), 7.91 (s, 1H).

Example 2

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine di-D-tartrate (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (810.18 mg) was dissolved in 8 mL of a D-tartaric acid-ethanol solution (751.13 mg/10 mL) with stirring at room temperature. The oil was precipitated when 2 mL of heptane was added. Accordingly, the oily substance was dissolved by ultrasonic treatment to prepare a clear solution. Several mg of crystals of the 1.5 D-tartrate prepared according to Example 1 were added, followed by stirring at room temperature. Stirring for about one hour resulted in gelation and subsequent precipitation of a solid. Further, stirring was continued while gradually adding 14 mL of heptane. A part of the suspension (2 mL) was separated and the solid was collected by filtration through a glass filter. The solid was dried under reduced pressure at room temperature to obtain 71.14 mg of the title compound as white solid crystals.

$^1$H-NMR (400 MHz, DMSO-$d_6$) δ (ppm): 1.97 (m, 1H), 2.15 (s, 3H), 2.16 (m, 2H), 2.30 (m, 1H), 3.98 (s, 3H), 4.28 (m, 2H), 4.29 (s, 4H), 4.51 (dd, J=9, 6 Hz, 1H), 7.22 (brs, 1H), 7.25 (brd, J=8 Hz, 1H), 7.27 (d, J=8 Hz, 1H), 7.32 (d, J=16 Hz, 1H), 7.46 (d, J=16 Hz, 1H), 7.49 (brdd, J=8 Hz, 1H), 7.61 (brdd, J=8 Hz, 1H), 7.77 (brd, J=8 Hz, 1H), 7.78 (d, J=8 Hz, 1H), 7.91 (brs, 1H).

Example 3

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Disulfate Concentrated sulfuric acid (11.5 μL) was added to a solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (98.09 mg) in ethanol (1 mL), and 1 mL of ethyl acetate was added with stirring at room temperature. Since the oily portion was confirmed on the bottom of the recovery flask, the oily substance was dissolved by ultrasonic treatment. Stirring at room temperature under shading for about 30 minutes resulted in precipitation of a solid. The solid was collected by filtration through a glass filter and dried under reduced pressure at room temperature to obtain 127.94 mg of the title compound as white solid crystals.

$^1$H-NMR (400 MHz, DMSO-$d_6$) δ (ppm): 1.97 (m, 1H), 2.17 (m, 2H), 2.30 (m, 1H), 2.34 (brd, J=1 Hz, 3H), 4.01 (s, 3H), 4.29 (m, 2H), 4.52 (dd, J=9, 6 Hz, 1H), 7.25 (brd, J=8 Hz, 1H), 7.37 (d, J=16 Hz, 1H), 7.40 (d, J=8 Hz, 1H), 7.50 (brdd, J=8 Hz, 1H), 7.55 (d, J=16 Hz, 1H), 7.61 (brdd, J=8 Hz, 1H), 7.77 (m, 1H), 7.78 (m, 1H), 8.00 (d, J=8 Hz, 1H), 9.36 (d, J=2 Hz, 1H).

Example 4

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Dihydrobromide Concentrated hydrobromic acid (24.8 μL) was added to a solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (51.42 mg) in ethanol (1 mL), and 1 mL of heptane was added with stirring at room temperature. After several minutes, 1 mL of heptane was further added to the solution and stirring was continued. The solution was stirred at room temperature for one hour and then further stirred at about 5° C. for 20 minutes. The precipitated solid was collected by filtration through a glass filter and dried under reduced pressure at room temperature to obtain 49.24 mg of the title compound as white solid crystals.

$^1$H-NMR (400 MHz, DMSO-$d_6$) δ (ppm): 1.99 (m, 1H), 2.17 (m, 2H), 2.30 (m, 1H), 2.34 (brd, J=1 Hz, 3H), 4.01 (s, 3H), 4.30 (m, 2H), 4.52 (dd, J=9, 6 Hz, 1H), 7.25 (brd, J=8 Hz, 1H), 7.37 (d, J=16 Hz, 1H), 7.40 (d, J=7 Hz, 1H), 7.50 (brdd, J=8 Hz, 1H), 7.55 (d, J=16 Hz, 1H), 7.61 (brdd, J=8 Hz, 1H), 7.77 (m, 1H), 7.78 (m, 1H), 8.00 (d, J=7 Hz, 1H), 9.37 (d, J=2 Hz, 1H).

Example 5

Synthesis of (8S)-2-{(E)-2-[6-methoxy-5-(4-methyl-1H-imidazol-1-yl)pyridin-2-yl]vinyl}-8-(2-trifluoromethylphenyl-5,6,7,8-tetrahydro-[1,2,4]triazolo[1,5-a]pyridine Hydrochloride Concentrated hydrochloric acid (3.6 μL) was added to a solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (19.80 mg) in 2-propanol (1 mL), and a total of 4 mL of heptane was added in 1 mL portions with stirring at room temperature. The solution was stirred at room temperature under shading for five days. The precipitated solid was collected by filtration through a glass filter and dried under reduced pressure at room temperature to obtain 7.45 mg of the title compound as white solid crystals.

$^1$H-NMR (400 MHz, DMSO-$d_6$) δ (ppm): 1.97 (m, 1H), 2.17 (m, 2H), 2.30 (m, 1H), 2.30 (s, 3H), 4.00 (s, 3H), 4.30 (m, 2H), 4.52 (dd, J=9, 6 Hz, 1H), 7.25 (brd, J=8 Hz, 1H), 7.36 (d, J=16 Hz, 1H), 7.37 (d, J=8 Hz, 1H), 7.50 (brt, J=8 Hz, 1H), 7.53 (d, J=16 Hz, 1H), 7.61 (brt, J=8 Hz, 1H), 7.66 (brs, 1H), 7.77 (brd, J=8 Hz, 1H), 7.96 (d, J=8 Hz, 1H), 9.06 (brs, 1H).

Example 6

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Hydrochloride Concentrated hydrochloric acid (14.3 µL) and heptane (7 mL) were added to a solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (79.77 mg) in 2-propanol (3 mL). A small amount of the crystals obtained in Example 5 were added as seed crystals with stirring at room temperature. The mixture was transferred to a low temperature laboratory at about 5° C. and stirred for one hour. Thereafter, 1 mL of heptane was further added, followed by stirring for several minutes. When the precipitated solid was collected by filtration through a glass filter, the solid was precipitated in the filtrate. The precipitated solid was collected by filtration through a glass filter and dried under reduced pressure at room temperature to obtain 38.02 mg of the title compound as white solid crystals.

$^1$H-NMR (400 MHz, DMSO-$d_6$) δ (ppm): 1.97 (m, 1H), 2.17 (m, 2H), 2.29 (m, 1H), 2.32 (brd, J=1 Hz, 3H), 4.00 (s, 3H), 4.30 (m, 2H), 4.52 (dd, J=9, 6 Hz, 1H), 7.25 (brd, J=8 Hz, 1H), 7.37 (d, J=16 Hz, 1H), 7.38 (d, J=8 Hz, 1H), 7.50 (brdd, J=8 Hz, 1H), 7.54 (d, J=16 Hz, 1H), 7.61 (brdd, J=8 Hz, 1H), 7.72 (brs, 1H), 7.77 (brd, J=8 Hz, 1H), 7.98 (d, J=8 Hz, 1H), 9.24 (brs, 1H).

Example 7

Synthesis of (8S)-2-{(E)-2-[6-methoxy-5-(4-methyl-1H-imidazol-1-yl)-pyridin-2-yl]vinyl}-8-(2-trifluoromethylphenyl)-5,6,7,8-tetrahydro-[1,2,4]triazolo-[1,5-a]pyridine Mesylate Mesylic acid (0.8 µL) was added to a mixed solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (50 mg) in t-butyl methyl ether (0.8 mL)-ethanol (0.1 mL). The mixture was solidified as a result of stirring at room temperature for two hours. The solid was collected by filtration through a glass filter. The solid was washed with t-butyl methyl ether-ethanol (8:1) and then dried under reduced pressure at room temperature to obtain 51.9 mg of the title compound as pale yellow solid crystals.

$^1$H-NMR (DMSO-$d_6$) δ (ppm): 1.90-2.05 (m, 1H), 2.10-2.22 (m, 2H), 2.28-2.40 (m, 1H), 2.31 (s, 3H), 2.35 (s, 3H), 4.02 (s, 3H), 4.25-4.39 (m, 2H), 4.50-4.55 (m, 1H), 7.27 (d, J=8.0 Hz, 1H), 7.38 (d, J=16.0 Hz, 1H), 7.41 (d, J=8.0 Hz, 1H), 7.51 (t, J=8.0 Hz, 1H), 7.55 (d, J=16.0 Hz, 1H), 7.63 (t, J=8.0 Hz, 1H), 7.78 (d, J=8.0 Hz, 1H), 7.79 (s, 1H), 8.01 (d, J=8.0 Hz, 1H), 9.37 (s, 1H).

Example 8

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Diphosphate A solution of phosphoric acid (52.8 mg) in acetonitrile (0.2 mL) was added to a solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (100 mg) in acetonitrile (0.8 mL) at room temperature. The precipitated oil was solidified as a result of stirring with spatula. The solid was collected by filtration through a glass filter. The solid was washed with ice-cold acetonitrile, air-dried at room temperature for 10 minutes and then dried under reduced pressure at room temperature to obtain 120 mg of the title compound as white solid crystals.

$^1$H-NMR (DMSO-$d_6$) δ (ppm): 1.90-2.05 (m, 1H), 2.11-2.20 (m, 2H), 2.15 (s, 3H), 2.25-2.35 (m, 1H), 3.99 (s, 3H), 4.24-4.39 (m, 2H), 4.50-4.55 (m, 1H), 7.23 (s, 1H), 7.26 (d, J=7.0 Hz, 1H), 7.28 (d, J=8.0 Hz, 1H), 7.33 (d, J=16.0 Hz, 1H), 7.47 (d, J=16.0 Hz, 1H), 7.51 (t, J=7.0 Hz, 1H), 7.63 (t, J=7.0 Hz, 1H), 7.78 (d, J=7.0 Hz, 1H), 7.79 (d, J=8.0 Hz, 1H), 7.90 (s, 1H).

Example 9

Synthesis of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Diphosphate A solution of phosphoric acid (13.2 mg) in ethanol (0.05 mL) was added to a mixed solution of (8S)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine (50 mg) in heptane (0.6 mL)-ethanol (0.15 mL) at room temperature. The reaction solution was stirred at room temperature, and the precipitated solid was collected by filtration through a glass filter. The solid was washed with heptane-ethanol (3:1) and then dried under reduced pressure at room temperature to obtain 37.6 mg of the title compound as white solid crystals.

$^1$H-NMR (DMSO-$d_6$) δ (ppm): 1.90-2.05 (m, 1H), 2.11-2.20 (m, 2H), 2.15 (s, 3H), 2.25-2.35 (m, 1H), 3.99 (s, 3H), 4.24-4.39 (m, 2H), 4.50-4.55 (m, 1H), 7.23 (s, 1H), 7.26 (d, J=7.0 Hz, 1H), 7.28 (d, J=8.0 Hz, 1H), 7.33 (d, J=16.0 Hz, 1H), 7.47 (d, J=16.0 Hz, 1H), 7.51 (t, J=7.0 Hz, 1H), 7.63 (t, J=7.0 Hz, 1H), 7.78 (d, J=7.0 Hz, 1H), 7.79 (d, J=8.0 Hz, 1H), 7.90 (s, 1H).

INDUSTRIAL APPLICABILITY

The present invention can provide various salts of the compound (1) including (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine 1.5 D-tartrate and (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine disulfate, and their crystals, which can be used as drug substances.

The invention claimed is:

1. A crystal of a salt comprising one acid selected from the group consisting of D-tartaric acid, sulfuric acid, methanesulfonic acid, hydrobromic acid, hydrochloric acid and phosphoric acid and (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine.

2. The crystal according to claim 1, wherein the crystal is (8S)-2-{(E)-2-[6-methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine 1.5 D-tartrate having diffraction peaks at diffraction angles (2θ±0.2°) of 12.6° and 23.2° in powder X-ray diffractometry.

3. The crystal according to claim 1, wherein the crystal is (8S)-2-{(E)-2-[6-methoxy-5-(4-methyl-1H-imidazol-1-yl)

pyridin-2-yl]vinyl}-8-[2-(trifluoromethyl)phenyl]-5,6,7,8-tetrahydro[1,2,4]triazolo[1,5-a]pyridine disulfate having diffraction peaks at diffraction angles (2θ±0.2°) of 17.1° and 24.0° in powder X-ray diffractometry.

* * * * *